US012678110B2

(12) United States Patent
Vancamberg et al.

(10) Patent No.: US 12,678,110 B2
(45) Date of Patent: Jul. 14, 2026

(54) SYSTEM AND METHOD FOR GENERATING PREDICTED VIEW FOR IMPROVED MAMMOGRAPHY IMAGING SYSTEM POSITIONING

(71) Applicant: GE Precision Healthcare LLC, Waukesha, WI (US)

(72) Inventors: Laurence Vancamberg, Poissy (FR); Clément Jailin, Antony (FR); Razvan Iordache, Clamart (FR); Kathleen Schindler, Fergus (CA)

(73) Assignee: GE Precision Healthcare LLC, Waukesha, WI (US)

( * ) Notice: Subject to any disclaimer, the term of this patent is extended or adjusted under 35 U.S.C. 154(b) by 170 days.

(21) Appl. No.: 18/526,780

(22) Filed: Dec. 1, 2023

(65) Prior Publication Data

US 2025/0176924 A1 Jun. 5, 2025

(51) Int. Cl.

| *A61B 6/04* | (2006.01) |
| *A61B 6/00* | (2006.01) |
| *A61B 6/42* | (2024.01) |
| *A61B 6/46* | (2024.01) |
| *A61B 6/50* | (2024.01) |

(52) U.S. Cl.
CPC .......... *A61B 6/0435* (2013.01); *A61B 6/4208* (2013.01); *A61B 6/4417* (2013.01); *A61B 6/465* (2013.01); *A61B 6/502* (2013.01); *A61B 6/5294* (2013.01); *A61B 6/547* (2013.01)

(58) Field of Classification Search
CPC ... A61B 6/0435; A61B 6/4208; A61B 6/4417; A61B 6/465; A61B 6/502; A61B 6/5294; A61B 6/547; A61B 6/0414; A61B 6/545
See application file for complete search history.

(56) References Cited

U.S. PATENT DOCUMENTS

| 7,558,367 B1 * | 7/2009 | Tinwala ................. G01G 19/52 |
| | | 378/37 |
| 7,732,775 B2 | 6/2010 | Kashiwagi |
| 7,974,378 B2 | 7/2011 | Fischer et al. |
| 8,135,199 B2 | 3/2012 | Russakoff |

(Continued)

FOREIGN PATENT DOCUMENTS

CN 110400302 B 11/2019

*Primary Examiner* — Kiho Kim
(74) *Attorney, Agent, or Firm* — Boyle Fredrickson, S.C.

(57) ABSTRACT

According to one aspect of an exemplary embodiment of the present disclosure, a radiography imaging system adapted to perform a diagnostic imaging procedure includes a radiation source, a detector adapted to receive radiation emitted from the radiation source to generate image data, a controller operably connected to the radiation source and the detector to control the operation of the radiation source and detector to generate the image data, the controller including a central processing unit and interconnected electronic memory unit for processing the image data from the detector, a display operably connected to the controller, and a user interface operably connected to the controller to enable user input to the controller. The radiography imaging system also includes an image prediction module operably connected to the controller and configured to receive a prior screening image of a patient, and generate a prediction view of the patient for presentation on the display.

20 Claims, 6 Drawing Sheets

(56)     References Cited

U.S. PATENT DOCUMENTS

| | | | |
|---|---|---|---|
| 10,357,216 B2 | 7/2019 | Sugiyama et al. | |
| 2007/0206844 A1 | 9/2007 | Russakoff et al. | |
| 2007/0274585 A1* | 11/2007 | Zhang | G16H 30/20 |
| | | | 382/132 |
| 2010/0080427 A1* | 4/2010 | Yeluri | G16H 30/20 |
| | | | 382/128 |
| 2011/0311026 A1* | 12/2011 | Lalena | G16H 40/63 |
| | | | 378/98.5 |
| 2015/0209599 A1* | 7/2015 | Schlosser | A61B 8/54 |
| | | | 600/427 |
| 2016/0235380 A1* | 8/2016 | Smith | A61B 6/463 |
| 2021/0401381 A1 | 12/2021 | Wells et al. | |
| 2022/0096037 A1 | 3/2022 | Fujimoto et al. | |
| 2023/0103969 A1 | 4/2023 | St. Pierre et al. | |

* cited by examiner

600

386

| RETRIEVE PRIOR SCREENING IMAGES | 602 |

382

| PROVIDE PRIOR SCREENING IMAGES AS INPUT | 604 |

| GENERATE PREDICTED *VIEW* FROM AI/MaL MODULE | 606 |

384

| OUTPUT PREDICTED VIEW ON DISPLAY | 608 |

ROC     LCC     RMLO     LMLO

44 / 350

386

386

386

386

400

382

402

COMPUTE PREDICTED VIEW

388

42

SYSTEM AND METHOD FOR GENERATING PREDICTED VIEW FOR IMPROVED MAMMOGRAPHY IMAGING SYSTEM POSITIONING

FIELD OF THE DISCLOSURE

The present disclosure relates generally to medical imaging systems, and more specifically to mammography imaging and biopsy systems.

BACKGROUND OF THE DISCLOSURE

Embodiments of the invention relate generally to X-ray medical imaging, and more particularly to devices, systems and methods employed to perform various imaging procedures, such as mammography imaging procedures including but not limited to spectral mammography (SM), such as 2D/3D dual-energy contrast-enhanced (CE) mammography exams, full-field digital mammography (FFDM) or digital breast tomosynthesis (DBT) mammography exams.

Spectral mammography (SM) is an X-ray imaging modality used to scan breasts for screening, diagnosis and/or interventional examinations. The effectiveness of spectral mammography is affected by numerous factors, one of which is the two-dimensional (2D) rendering of images obtained using SM.

Alternative systems to SM are also known for breast imaging. Some examples include full-field digital mammography, which captures the image directly onto a flat-panel detector, computed radiography, which involves the use of a cassette that contains an imaging plate, or digital breast tomosynthesis (DBT). A digital breast tomosynthesis (DBT) or mammography-tomography (mammo-tomo) system is a dedicated mammography system that acquires several (e.g., tens of) angularly offset projection X-ray images and uses the resulting X-ray image data to reconstruct three-dimensional (3D) image datasets.

The 3D image datasets are used to form various volumetric representations of the imaged breast, including an entire 3D volume of the breast, and various 3D sections of the 3D volume, such as slices or slabs constituting specified thicknesses of the 3D volume oriented to provide the desired view of one or more region(s) of interest (ROI) detected within the 3D image dataset.

In addition, when the 3D image datasets of the breast have been produced, after being utilized in a suitable diagnosis procedure, they can be utilized to guide a biopsy device employed with the DBT system into the breast to obtain a biopsy of the region of interest (ROI) identified within the 3D image datasets. In DBT systems, the biopsy device is disposed directly on the DBT system in order to be able to perform the biopsy utilizing the 3D image dataset or to use a stereo-pair of camera images of the breast and biopsy device with a subsequent triangulation of the biopsy device to the ROI in the breast to guide the biopsy device to the ROI.

With regard to the use of these mammography imaging systems, in an initial screening imaging procedure, the breast of the patient will be imaged in a number of standardized views, including but not limited to a craniocaudal (CC) view and a mediolateral oblique (MLO) view. The images of these two views obtained by the mammography imaging system can be reviewed to determine the presence of any lesions, calcifications, or other ROI within the breast. If any such ROI are located, the patient can be recalled for a subsequent diagnostic imaging procedure to obtain additional breast images such spot compression (SPOT) or magnified (MAG) views obtained in corresponding imaging procedures, or even to perform a biopsy of the ROI identified within the breast in the screening images, i.e., the CC and MLO images.

As on many occasions significant time elapses between the screening imaging procedure and the diagnostic imaging procedure, e.g., the MAG imaging procedure and/or the biopsy procedure, the patient must be repositioned on the mammography imaging system in order to perform the MAG and/or biopsy procedure. In each of these types of procedures, images are obtained of the ROI within the breast when repositioned on the mammography imaging system. However, in each diagnostic procedure the area imaged by the mammography imaging system is focused on the ROI, such that the radiation source of the mammography imaging system images a much smaller area of the breast than in the screening imaging procedures.

As a result of imaging the much smaller area(s) within the breast containing only the ROI in the diagnostic imaging procedures, it is necessary to accurately position the breast on the mammography imaging system to align the ROI within the field of view of the radiation source (FoV). More specifically, the diagnostic imaging procedures, e.g., the MAG procedure and/or the biopsy procedure, often require the acquisition of a lateromedial (LM) and/or mediolateral (ML) view of the breast before the procedure, in order to reliably assess the location of the ROI within the breast, including estimation of the distance with respect to anatomical landmarks like the nipple, and thus allowing a proper position of the ROI within the FOV for the diagnostic imaging procedure.

However, an ML/LM view may not be available at the time of the diagnostic imaging procedure. In this situation, the only information available to the technologist on the location of the ROI is the ROI position in the CC and/or MLO views. To place the ROI in within the FoV, the technician must mentally/manually estimate or guess where the ROI would have been located in a LM/ML view, in particular in regards to landmarks on the breast, e.g., the nipple.

The technique used to mentally/manually estimate the position of the is called triangulation of breast lesion(s) and is described, along with a discussion of the frequent misapplication of the technique, in *Triangulation of Breast Lesions: Review and Clinical Applications*. Jeong Mi Park, MD, and Edmund A. Franken Jr. Because the process of performing the triangulation of breast lesion(s) makes certain assumptions regarding the configuration of the breast, and is often applied incorrectly, multiple diagnostic images (SPOT, MAG, biopsy) must often be obtained to properly position the ROI for the diagnostic procedure, greatly decreasing the effectiveness and comfort for the patient, while significantly increasing the time required for the performance of the diagnostic procedure.

Therefore, with regard to the set up and performance of diagnostic imaging procedures on mammography imaging systems, particularly concerning SPOT, MAG and biopsy imaging and/or diagnostic procedures, it is desirable to develop a system and method for accurately determining the position of ROI within a breast for proper alignment of the ROI within the FoV using only information already available from CC and MLO views obtained in a screening imaging procedure previously performed on the breast.

SUMMARY OF THE DISCLOSURE

According to one aspect of an exemplary embodiment of the present disclosure, a radiography imaging system adapted to provide patient position assistance when performing a diagnostic imaging procedure includes a radiation source, a detector adapted to receive radiation emitted from the radiation source to generate image data, a controller operably connected to the radiation source and the detector to control the operation of the radiation source and detector to generate the image data, the controller including a central processing unit and interconnected electronic memory unit for processing the image data from the detector, a display operably connected to the controller for presenting images formed from the image data, a user interface operably connected to the controller to enable user input to the controller, and an image prediction module operably connected to the controller and configured to receive a prior screening image of a patient, and generate a predicted view of the patient for presentation on the display. The predicted view is a simulated image/illustration of the breast in a predefined view (ML, LM, or other view).

According to still another aspect of an exemplary embodiment of the present disclosure, a biopsy positioner adapted to be secured to a medical imaging system for performing a biopsy procedure thereon includes a base adapted to be engaged with a support structure on the medical imaging system, and a positioning arm connected to the base, the positioning arm including a first arm moveably connected to the base and a second arm moveably connected to the first arm, wherein the first arm is moveable between lateral positions on opposed sides of the base.

According to still another aspect of an exemplary embodiment of the present disclosure, a method for providing patient positioning assistance to perform a diagnostic imaging procedure on a radiography imaging system includes the steps of providing a radiography imaging system having a radiation source, a detector, a controller operably connected to the radiation source and the detector to control the operation of the radiation source and detector to generate image data, the controller including a central processing unit and interconnected electronic memory unit for processing the image data from the detector, a display operably connected to the controller for presenting images formed from the image data, a user interface operably connected to the controller to enable user input to the controller, and an image prediction module operably connected to the controller and configured to generate a prediction view of the patient for presentation on the display from one or more prior screening images of the patient, supplying the one or more prior screening images to the image prediction module, generating the predicted view of the patient, and presenting the predicted view of the patient on the display.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Further, while the embodiments disclosed herein are described with respect to a mammography apparatus for the 2-dimensional imaging of breast tissue, it is to be understood that embodiments of the invention may be applicable to other types of imaging devices for both 2-dimensional and 3-dimensional imaging including, for example, fluoroscopy, full-filed digital mammography, digital breast tomosynthesis (DBT) and spectral mammography (single or multi-energy), as well as for imaging procedures for tissue other than breast tissue. Further still, embodiments of the invention may be used to analyze tissue, generally, and are not limited to analyzing human tissue.

Figure 1:
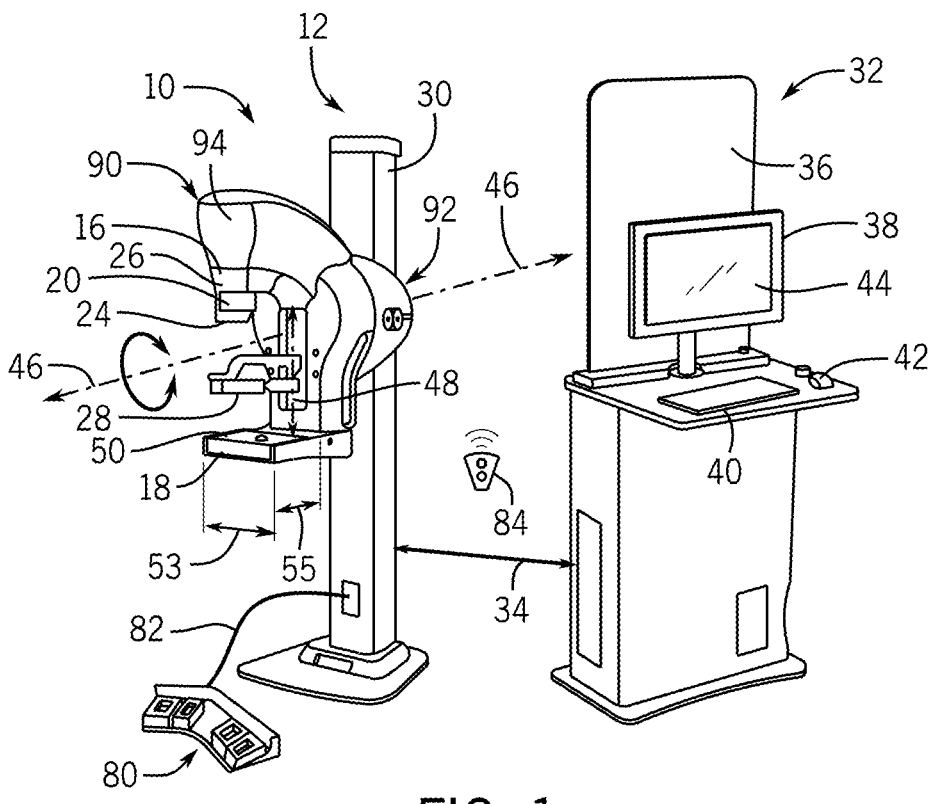
FIG. 1 is a perspective view of a radiography imaging device in the form of a mammography imaging system for imaging the breast tissue of a patient, in accordance with an embodiment of the disclosure.
Figure 2:
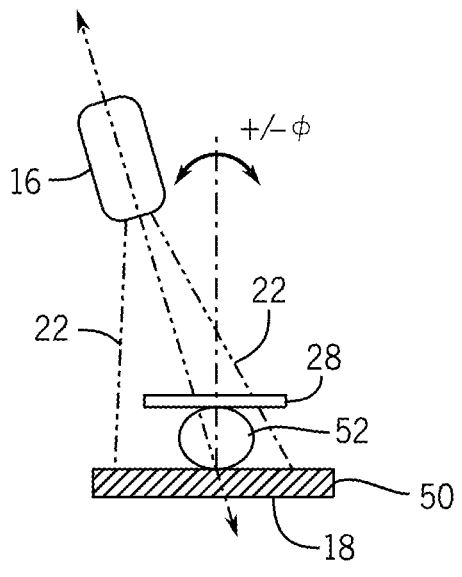
FIG. 2 is a diagram of the system of FIG. 1, showing the radiation source of the mammography imaging system in a scanning position, in accordance with an embodiment of the disclosure.

Referring now to FIGS. 1 and 2, the major components of an exemplary radiography imaging system 10 formed as a mammography device or system 12 for imaging breast tissue according to an embodiment of the invention are shown. The mammography system 12, such that disclosed in US Patent Application Publication No. US20200060632, entitled Apparatus And Method For Mammographic Breast Compression, and U.S. patent application Ser. No. 18/110,062 entitled Mammography Imaging System with Universal Attachment Structures, the entirety of which are each expressly incorporated herein by reference for all purposes, includes a radiation source/x-ray source 16, a radiation detector 18, and a collimator 20. The radiation source 16 is movable between a variety of imaging positions relative to the detector 18, and is operative to emit radiation rays 22 (FIG. 2) that are received by the radiation detector 18 to provide an image of an object, such as a breast 52. In embodiments, the mammography system 12 may include a patient shield 24 mounted to the radiation source 16 via face shield rails 26 to prevent the patient's head from obstructing the radiation rays and protecting the patient from the radiation rays 22.

Referring still further to FIGS. 1 and 2, the mammography system 12 also includes a compression paddle or plate 28 and a support structure 30 to which one or more of the radiation source 16, radiation detector 18, and/or compression plate 28 are mounted. In embodiments, the mammography system 12 may further include a controller 32. The controller 32 may be a workstation having at least one processor/central processing unit/computer and a memory device/database that stores information and/or instructions for the operation of the system 10 that are employed by the controller 32, as shown in FIG. 1 or, in other embodiments, the controller 32 may be embedded/integrated into one or more of the various components of the mammography system 12 disclosed above. In embodiments, the controller 32 may be in electrical communication with the radiation source 16, radiation detector 18, and/or the compression plate 28 via a cable 34. As will be appreciated, in embodiments, the connection 34 may be a wireless connection. In embodiments, the controller 32 may include a radiation shield 36 that protects an operator of the mammography system 12 from the radiation rays 22 emitted by the radiation source 16. The controller 32 may further include a display 38, a keyboard 40, mouse 42, and/or other appropriate user input devices that facilitate control of the system 10 via a user interface 44.

As further shown in FIGS. 1 and 2, the radiation source 16, along with the radiation detector 18, forms part of an x-ray system which provides x-ray imagery for the purpose of imaging a body part of a patient, such as breast 52. As stated above, the radiation source 16 emits the radiation rays 22 such that the radiation rays 22 travel from the radiation source 16 to the radiation detector 18. While the radiation rays 22 are discussed herein as being x-rays, it is to be understood that the radiation source 16 may emit other types of electromagnetic rays which can be used to image a patient. The radiation source 16 may be mounted to the support structure 30 such that the radiation source can rotate around an axis 46 in relation to the radiation detector 18, although movement of the radiation source 16 in paths other than rotation about a fixed axis, such as during digital breast tomosynthesis (DBT), are also envisioned. In embodiments, the radiation detector 18 may be configured to rotate or translate within its housing, such as in the directions indicated by arrows 53 and 55.

In the illustrated exemplary embodiment of FIG. 1 the radiation source 16 and the detector 18 are mounted to a gantry 90 that is secured to the support structure 30. The support structure 30 houses a translation mechanism 92 that is operably connected to the gantry 90. The translation mechanism 92 is operable to move the gantry 90 vertically with respect to the support structure 30 in order to position the gantry 90 at the appropriate height to accommodate the dimensions of the patient on which the mammography system 12 is being utilized. The translation mechanism 92 is also operable to rotate the gantry 90 relative to the support structure 30 about the horizontal axis 46 in order to position the gantry 90 rotationally with regard to the patient, as necessary.

The gantry 90 includes a generally C-shaped body 94 with the radiation source 16 at one end and the detector 18 at the opposite end. In this configuration, regardless of the vertical and/or rotational orientation of the gantry 90, such as to position the radiation source 16 and detector 18 relative to the patient breast 52 to obtain x-ray images at various orientations, such as for craniocaudal (CC), mediolateral oblique (MLO) or mediolateral (ML)/lateromedial (LM) views, among others, the radiation source 16 is disposed in the required alignment relative to the detector 18. In this position, the detector 18 is capable of receiving the x-rays 22 emitted from the radiation source 16 that pass through the portion of the patient, i.e., patient breast 52, located between the radiation source 16 and the detector 18 in order to generate image data for transmission to the control system 32 of the mammography device/system 10 to create/reconstruct a 2D and/or 3D images or image dataset for viewing by a physician, such as by using DBT, among other known methods.

Additionally, in another embodiment the radiation source 16 can be attached to the gantry 90 to rotate and/or move independently of the gantry 90 and detector 18 in order to enable the radiation source 16 to take x-ray images of the patient breast at various angles relative to the detector 18, e.g., between +/−90°. The images obtained between these angles for the radiation source 16 can be used either for creation of 2D and/or 3D images when operating the mammography system 12 in a screening imaging procedure or imaging mode, or a diagnostic imaging procedure or imaging mode, e.g., in one or more of a spot compression (SPOT), a magnification (MAG) or biopsy imaging procedure or imaging mode.

As stated above, the radiation detector 18 receives the radiation rays 22 emitted by the radiation source 16. In embodiments, data regarding the radiation rays 22 received by the radiation detector 18 may be electrically communicated to the controller 32 from the radiation detector 18 via cable/electronic connection 34 such that the controller 32 generates one or more 2D and/or 3D images which may be shown on the display 38 and stored in the memory device.

The compression plate 28 is operative, in response to instruction from the controller 32 or in response to instructions from controller(s) on or near the mammography system 10, such as remote control, 84, or switch controllers 80 connected by cable 82, to move towards and away from the radiation detector 18 as indicated by arrows/compression axis 48 such that the compression plate 28 flattens and holds a body part, e.g., breast 52, in place against the surface 50 of the radiation detector 18. In this respect, the radiation detector 18 and in particular the surface 50 thereof is referred to herein as a "compression surface or support plate" that cooperates with the compression plate 28 to compress and clamp a breast of a patient therebetween.

Figure 3:
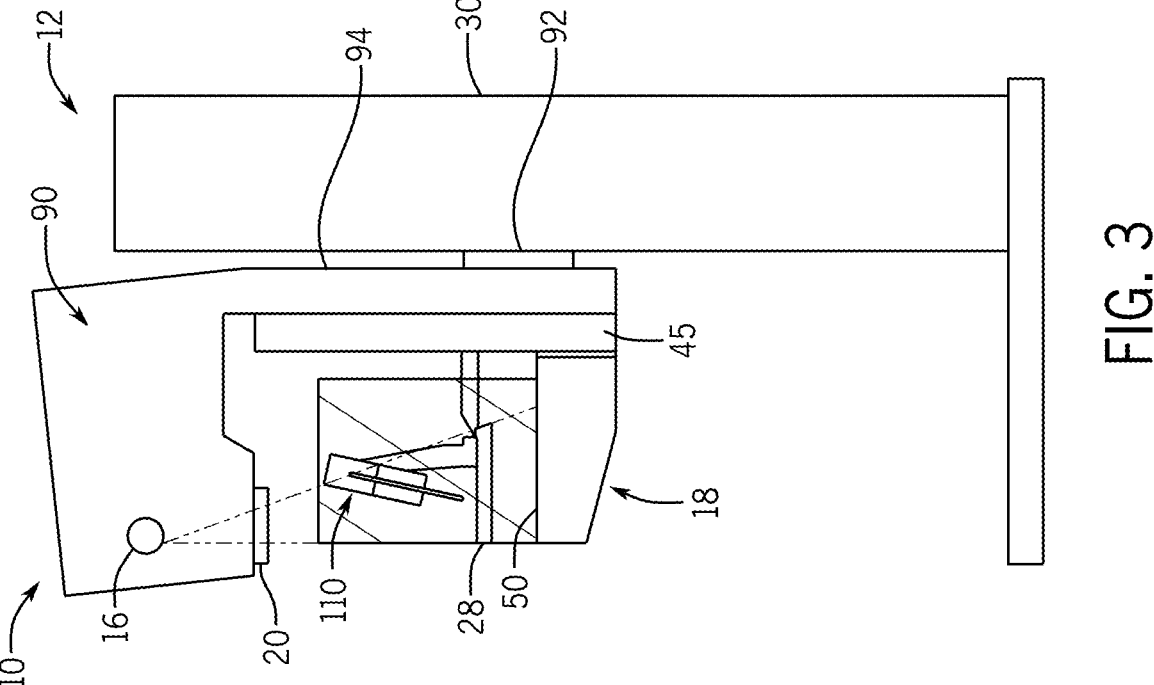
FIG. 3 is an isometric view of the mammography imaging system of FIG. 1 including a biopsy device secured to the mammography system, in accordance with an embodiment of the disclosure.

Referring now to FIG. 3, in one exemplary embodiment of the disclosure, a biopsy device 110 is attached to the mammography system 12, such as to the gantry 90, in a known manner. The biopsy device 110 is present in order to allow the mammography system 12 to perform a diagnostic biopsy procedure, e.g., where the movement of the biopsy device 110 is guided by images of the breast 52 obtained by the mammography imaging system 12. Further, with regard to another exemplary embodiment shown in FIG. 4, a magstand 112 can be positioned on the surface 50 in order to locate a breast 52 engaged thereon closer to the radiation source 16. The position of the breast 52 closer to the radiation source 16 on the magstand 112 enables magnified images of the breast 52 to be obtained using the mammography system 12 in a diagnostic MAG imaging mode for the mammography imaging system 12.

Figure 4:
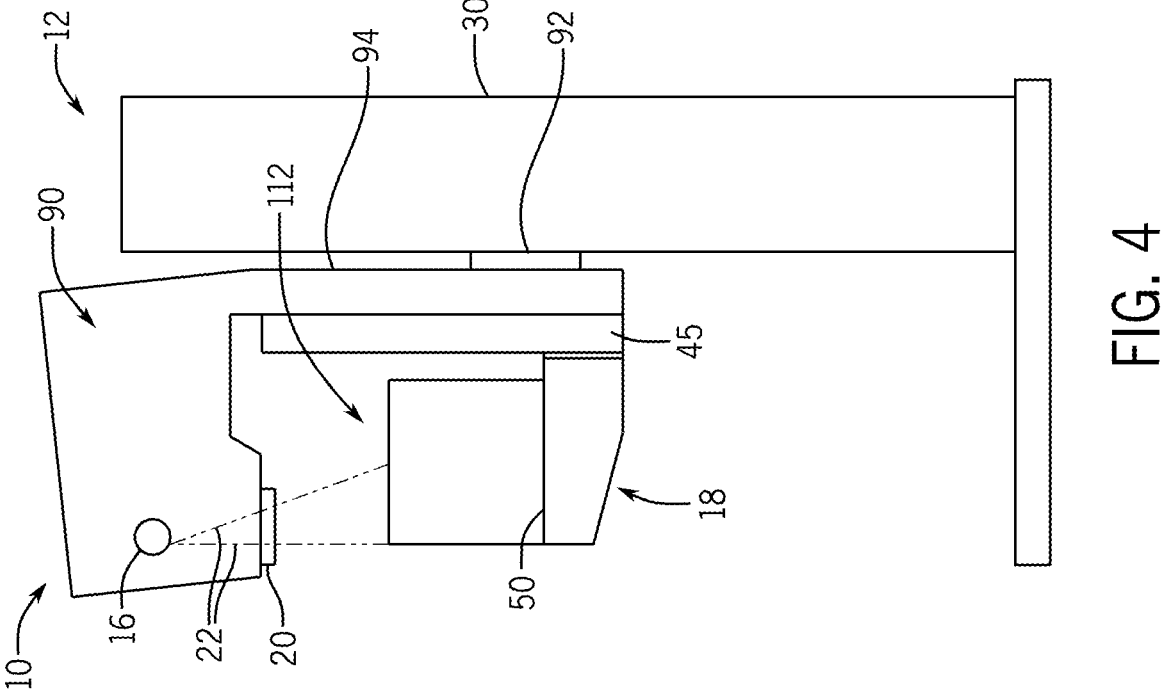
FIG. 4 is an isometric view of the mammography imaging system of FIG. 3 including a magnification stand secured to the mammography imaging system, in accordance with an embodiment of the disclosure.
Figure 5:
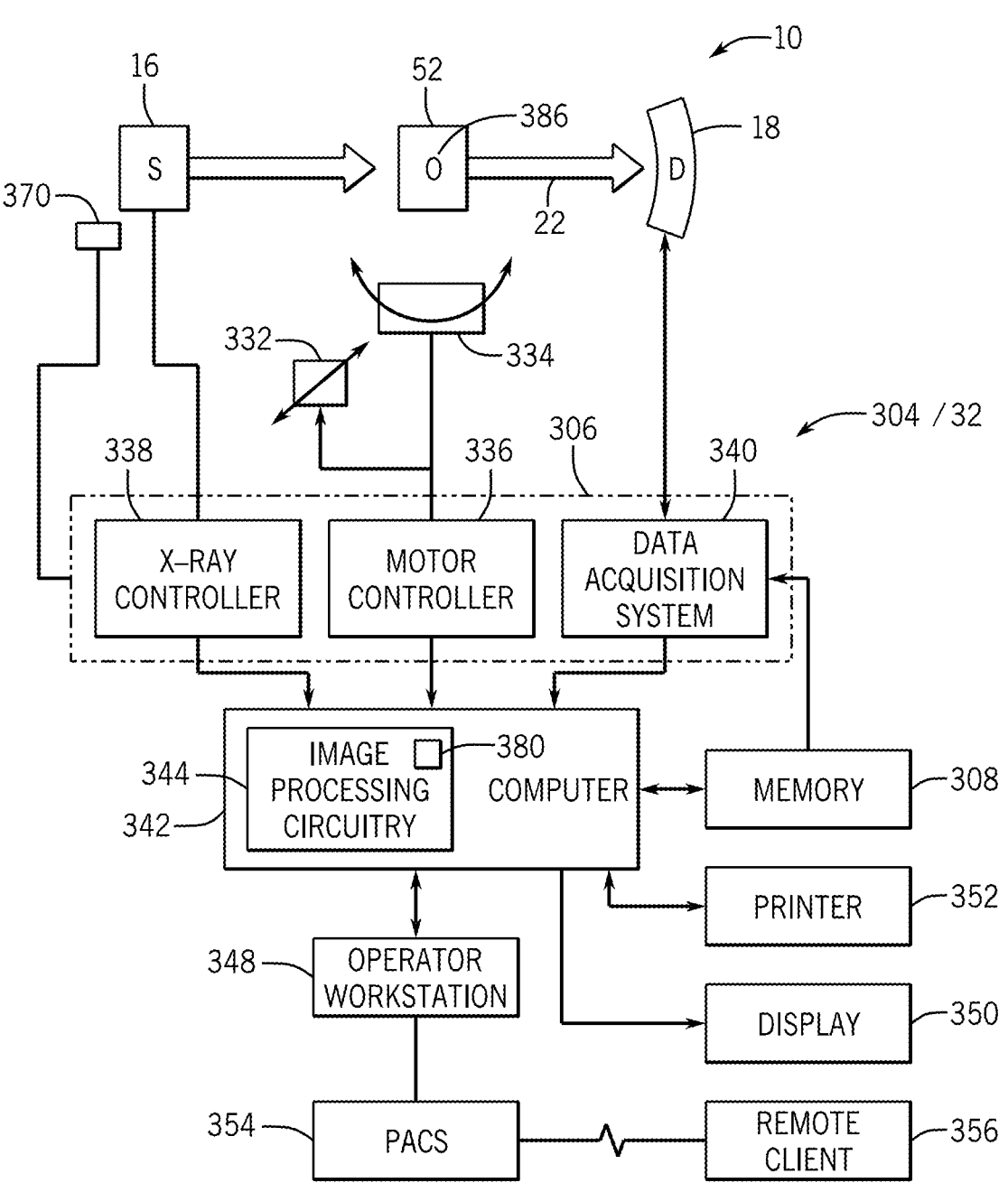
FIG. 5 is a schematic view of the mammography imaging system of FIG. 1 including an image prediction module, in accordance with an embodiment of the disclosure.

In order to facilitate the employment of the mammography imaging system 12 to perform the diagnostic imaging procedures using the configurations shown in FIGS. 3 and 4, as shown in FIG. 5 the mammography imaging system 12 includes a control device 304 illustrated as part of the controller 32 and including a control processor 306, an electronic memory 308 for storing operating instructions for the control processor 306, among other information. However, embodiments where the control device 304 and/or control processor 306 is separate from other control devices, e.g., controller 32 or other control circuitry local or remote to the mammography imaging system 12, are also encompassed by the present disclosure, such that the function(s) of the control device 304 can optionally be performed in part by or separately from the controller 32.

The control processor 306 can command operation of the mammography imaging system 12 to execute filtration, examination and/or calibration protocols and may process the acquired data. With respect to the radiation source 16, the control device 304, optionally in coordination with the controller 32, furnishes power, focal spot location, control signals and so forth, for the X-ray examination sequences. In accordance with certain embodiments, the control device 304 may control operation of the gantry 90 (or other structural support to which the radiation source 16 and detector 18 are attached), and/or the translation and/or inclination of the patient support over the course of an examination.

In addition, as shown in the illustrated embodiment of FIG. 5, the control processor 306, via a motor controller 336, may control operation of a linear positioning subsystem 332 and/or a rotational subsystem 334 used to move components of the mammography imaging system 12. The control processor 306 may include signal processing circuitry and associated memory circuitry, such as electronic memory 308. In such embodiments, the memory circuitry 308 may store programs, routines, and/or encoded algorithms executed by the control processor 306 to operate the mammography imaging system 12, including the X-ray source 16 and to process the digital measurements acquired by the detector 18 in accordance with the steps and processes discussed herein. In one embodiment, the control processor 306 may be implemented as all or part of a processor-based system.

The radiation source 16 may be controlled by an X-ray controller 338 contained within the control processor 306. The X-ray controller 338 may be configured to provide power, timing signals, and/or focal size and spot locations to the radiation source 16. In addition, in some embodiments the X-ray controller 338 may be configured to selectively activate the radiation source 16 such that tubes or emitters at different locations within the mammography imaging system 12 may be operated in synchrony with one another or independent of one another or to switch the source between different energy profiles during an imaging session.

The control processor 306 may include a data acquisition system (DAS) 340. The DAS 340 receives data collected by readout electronics of the detector 18, such as digital signals from the detector 18. The DAS 340 may then convert and/or process the data for subsequent processing by a processor-based system, such as a computer 342 operably connected to the control processor 306. In certain implementations discussed herein, circuitry within the detector 18 may convert analog signals of the detector to digital signals prior to transmission to the data acquisition system 340. The computer 342 may include or communicate with one or more non-transitory memory devices 308 that can store data processed by the computer 342, data to be processed by the computer 342, or instructions to be executed by image processing circuitry 344 of the computer 342. For example, a processor of the computer 342 may execute one or more sets of instructions stored on the memory 308, which may be a memory of the control device 304, the computer 342, or other memory of the processor, firmware, or a similar instantiation, to perform image acquisition and reconstruction techniques and/or processes.

The computer 342 may also be adapted to control features enabled by the control processor 306 (i.e., scanning operations and data acquisition), such as in response to commands and scanning parameters provided by an operator via the user interface 310 and/or operator workstation 348. Further, the display 44/350 and/or the printer 352 coupled to the control device 304 and user interface 310 allows the operator to view relevant system data, imaging parameters, raw imaging data, reconstructed data (e.g., soft tissue images, bone images, segmented vascular trees, and so on), material basis images, and/or material decomposition, and so forth. Further, the control processor 306 may include or be coupled to a memory or picture archiving and communications system (PACS) 354. PACS 354 may be coupled to the computer 342 directly and/or to a remote system or client 356, radiology department information system (RIS), hospital information system (HIS) or to an internal or external network, so that others at different locations can gain access to the image data.

Figures 6, 7:
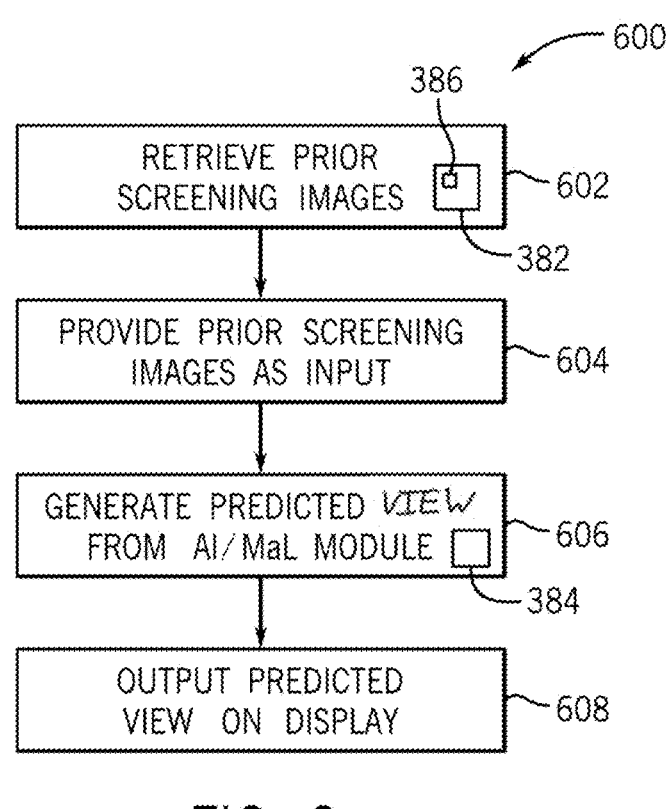
FIG. 6 is a schematic view of a first embodiment of a method of operation of the image prediction module of FIG. 5, in accordance with an embodiment of the disclosure.
FIG. 7 is a schematic view of a display of the mammography imaging device of FIG. 1, in accordance with an embodiment of the disclosure.

In the exemplary embodiment of the mammography imaging system 12 and method operation in FIGS. 5 and 6, to enhance the ability of the mammography imaging system 12 to perform diagnostic imaging procedures in follow up to one or more screening imaging procedures performed using the mammography imaging system 12 and/or a separate medical imaging system, one or more of the controller 32, the control processor 306, and/or the image processing circuitry 344 in the computer 342 can include an artificial intelligence AI and/or machine learning (MaL) algorithm forming an image prediction module 380 trained to analyze one or more prior screening images 382 of the breast 52 stored in PACS 354, and configured to generate one or more predicted view(s) 384 of the breast 52 on the mammography imaging system 12 that are utilized when performing a subsequent diagnostic imaging procedure the breast 52, which can be defined as an imaging procedure performed subsequent to the screening procedure and focusing on obtaining any local view or image of one or more ROIs 386 identified within the breast 52 in the images from the screening imaging procedure. The image prediction module 380 operates to review the one or more prior screening image(s) 382 provided as an input to the image prediction module 380 to create as the predicted view 384 an artificial or synthetic image 385 of the breast 52 in the position optimized for the imaging of the ROIs 386 identified within the screening image(s) 382, that is representative of the image view(s) of the breast 52 to be obtained in the performance of the diagnostic imaging procedure.

In an exemplary embodiment, after the creation of the prior screening image(s) 382, and optional storage in PACS 354, such as one or more radiography images of the breast 52, including but not limited to a CC image 400 and/or a MLO image 402, or images of the breast 52 from other imaging modalities, such as an ultrasound (US) image, a magnetic resonance (MRI) image or other type(s) of imaging modalities, the image prediction module 380 operates to generate a predicted or synthetic ML or LM view 385 of the breast 52 similar to that to be obtained in the subsequent diagnostic imaging procedure using the prior screening images 382. The synthetic ML or LM view 385 generated by the image prediction module 380 provides a representation of the proper orientation or position of the breast 52 on the mammography imaging system 12 in order to dispose the ROIs 386 identified within the prior screening image(s) 382, e.g., microcalcifications, cysts, solid masses, etc., or other regions of clinical relevance present within the prior screening image(s) 382, in the optimal location for the imaging of the ROIs 386 in the views to be obtained in the subsequent diagnostic imaging process. For example, traditional image processing techniques, or Artificial Intelligence (AI) based-approaches including machine learning (MaL) and deep learning (DL), among others, or a combination of both can be used to create a synthetic ML and/or LM view 385 of the breast 52 from the prior screening image 382(*s*). For AI based identification approaches the end goal of identifying ROIs 386 in the prior screening image(s) 382 and forming the synthetic ML and/or LM view(s) 385 could be formulated as either image segmentation or object localization problem. Though MaL based approaches like support vector machines (SVM), random forest (RF), etc., can be used to solve these problems, generative deep learning models e.g. convolutional neural networks (CNN), a class of DL based models, are best suited for such tasks yielding much better accuracy and adaptability across various imaging conditions. Additionally, with the identification and localization of ROIs 386 and other landmarks, e.g., the nipple 394 (FIG. 9), present within the prior screening image(s) 382 by the image prediction module 380, the image prediction module 380 can output the results, e.g., the predicted views 384, including but not limited to the synthetic ML and/or LM view 385 of the breast(s) 52, to assist in positioning the breast 52 on the mammography imaging system 12 for a subsequent diagnostic imaging procedure, along with optional visual indications 387 (FIG. 9) on the synthetic ML/LM view 385 of the location of the ROI(s) 386 therein.

Figures 8, 9:
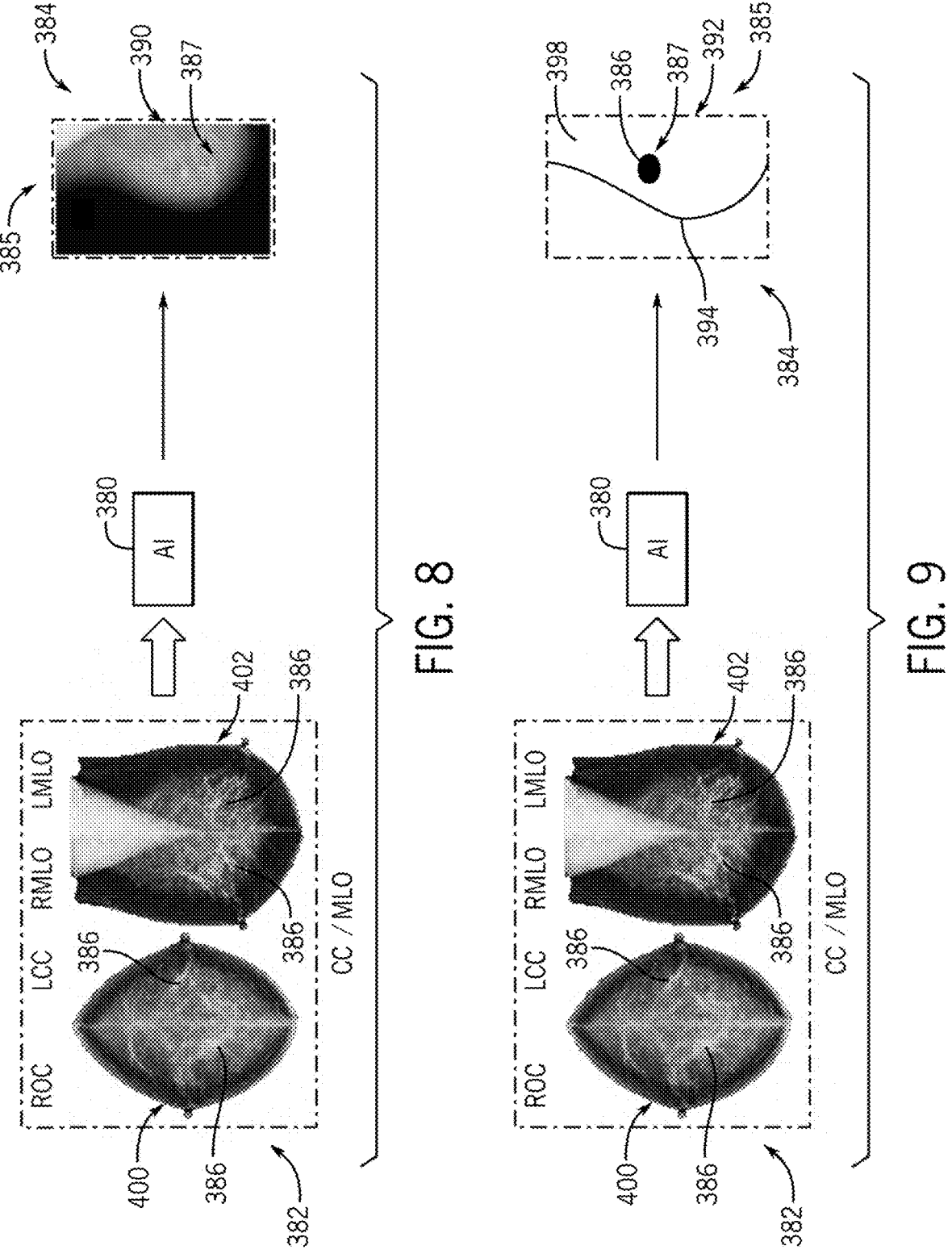
FIG. 8 is a schematic view of a first embodiment of the method of FIG. 6, in accordance with an embodiment of the disclosure.
FIG. 9 is a schematic view of a second embodiment of the method of FIG. 6, in accordance with an embodiment of the disclosure.

With respect to exemplary forms for the image prediction module 380, the image prediction module 380 can be a part of a DL/image processing algorithm pipeline, where the initial image processing performed in the image processing circuitry 344 detects the nipple 394 (FIG. 9) and the skin line 396 (FIG. 9), with the image prediction module 380 utilizing these located features in the prior screening image(s) 382 for use in predicting the geometric image(s) 392 (FIG. 9) and/or synthetic radiographic view 390 (FIG. 8). Further, with regard to the training of the image prediction module 380 for one or the generation of the predicted views 384, the image prediction module 380 can be provided with sets of CC/MLO images of a breast or other body part, as well as images of the same breast using other imaging modalities, e.g., US, MRI, etc., as inputs that are compared with a desired view of the breast, e.g., an ML and/or LM view, forming the ground truth for comparison of the output image(s) or view(s) from the image prediction module 380.

With particular reference to FIG. 6, in an exemplary embodiment of the method 600 of operation of the image prediction module 380, initially in step 602 the one or more prior screening image(s) 382 are retrieved from an electronic storage or memory, such as PACS 354. In step 604 the one or more prior screening images 382 are provided as an input to the image prediction module 380. The process in steps 602 and 604 of retrieving and providing the prior screening image(s) 382 as the input can be performed automatically by the controller 32, the control processor 306, and/or the image processing circuitry 344, such as immediately upon completion of a screening imaging procedure using the mammography imaging system 12, or can be manually performed. In an exemplary embodiment of a manual operation to provide the prior screening image(s) 382 to the image prediction module 380, as shown in FIG. 7, the prior screening image(s) 382 can be presented on the display 44/350 after acquisition with or retrieval from the mammography imaging system 12 along with an icon 388 on the display 44/350 representing the activation of the image prediction module 380. Upon selecting the icon 388 for manual retrieval, such as by selecting the icon 388 with the user interface 40, 42, or automatic initiation of the retrieval, the prior screening image(s) 382 are retrieved from memory 308 and/or PACS 354 and supplied or provided to the image prediction module 380. In addition to the prior screening image(s) 382, the input 604 can include information on the operating parameters for the mammography imaging system 12 when the prior screening image(s) 382 were obtained, such as field of view (FoV) and compression force, metadata for the prior screening image(s) 382, including the angles at which the prior screening image(s) 382, e.g., CC and MLO images of one or both of a right and left breast 52, were obtained, as well as lesion location information as provided by annotation(s) added to the prior screening image(s) 382 manually or by computer automatic detection (CAD) systems associated with the mammography imaging system 12.

Upon receiving the one or more prior screening image(s) 382, the image prediction module 380 proceeds, e.g., automatically, in step 606 to generate the predicted view 384 of the breast 52 or other body portion represented in the prior screening image(s) 382 which is provided in step 608 as the output from the image prediction module 380. As illustrated in the exemplary embodiment of FIG. 8, the output 608 of the predicted view 384 can take the form of an actual predicted radiography image 390 of the body portion, e.g., breast 52, to be obtained in the subsequent diagnostic imaging procedure, or can be a generalized geometrical image 392 as shown in FIG. 9. With the predicted radiography image 390, the representation of the breast 52 corresponds to an actual predicted radiography view of the selected image of the breast 52 to be obtained by the mammography imaging system 12 in the subsequent diagnostic imaging procedure, such as an ML or an LM image. The geometrical image 392 provides a generalized representation of the breast 52, including at least, the ROI(s) 386, the nipple 394, the skin line representation 396 and the pectoral muscle 398.

In either form, the predicted view 384 can be presented to the user on the display 44/350 in association with the prior screening image(s) 382 in order to review the information provided in each of the predicted view 384 and the prior screening image(s) 382. The predicted views 384 and the prior screening image(s) 382 can be presented to the user, optionally nipple-aligned with one another, to facilitate a review of the correspondence between the predicted views 384 and the prior screening image(s) 382 and the proper positioning of the patient on the mammography imaging system 12 for performance of the diagnostic imaging procedure, e.g., biopsy of MAG procedure.

Figure 10:
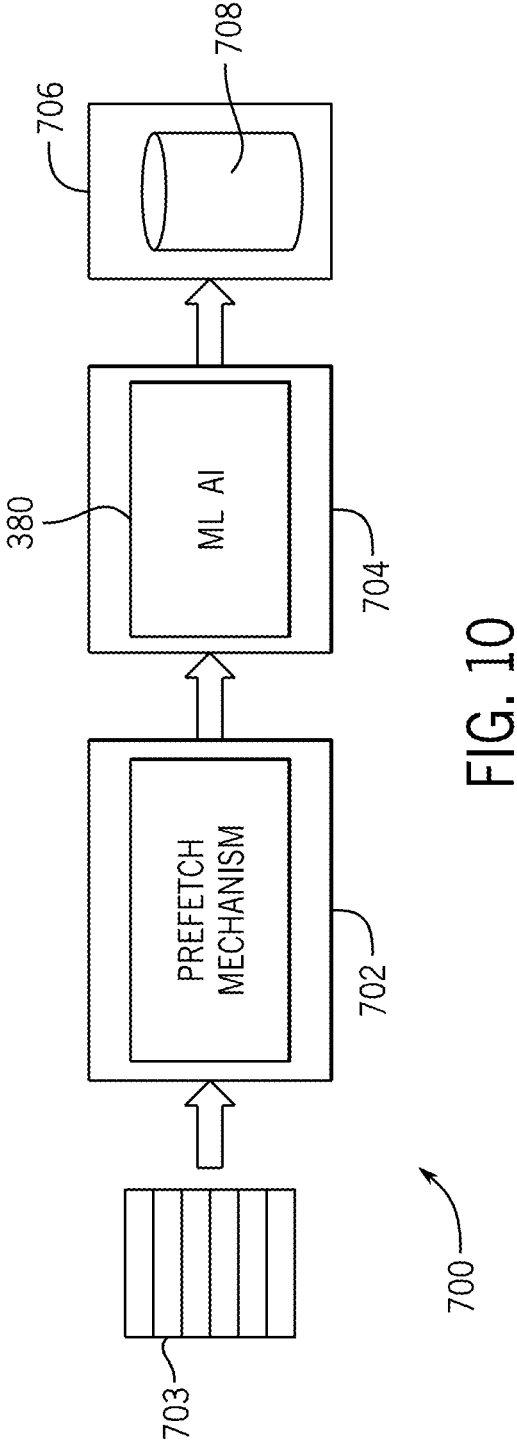
FIG. 10 is a schematic view of a second embodiment of a method of operation of the image prediction module of FIG. 5, in accordance with an embodiment of the disclosure.

Looking now at FIG. 10, in another exemplary embodiment of the method 700 of operation of the image prediction module 380, in step 702 a prefetch image retrieval request from a worklist or schedule of patients 703 is made to access the prior screening image(s) 382 stored in association with a patient file, such as stored in memory devices 308 and/or PACS 354, prior to performing a diagnostic imaging procedure on the patient. In step 702, the prior screening image(s) 382 from any image modality associated with the selected patient are accessed and provided to the image prediction module 380 as inputs. In step 704 the image prediction module 380 operated to generate one or more predicted views 384 of the body part of the patient that is to be the subject of the subsequent diagnostic imaging procedure. The one or more predicted views 384 are provided as output 707 from the module 380 and stored in a database 708 in step 706. When the patient associated with the predicted view(s) 384 is being prepared for the diagnostic imaging procedure, the predicted view(s) 384 can be accessed from the database 708 by the user of the radiography imaging system 10, optionally along with the prior screening image(s) 382, for review on the display 44/350 to properly position the patient on the radiography imaging system 10 for imaging the ROIs 386 prior to initiating the subsequent diagnostic imaging procedure on the patient.

It is understood that the aforementioned apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A radiography imaging system adapted to provide patient position assistance when performing a diagnostic imaging procedure, the radiography imaging system comprising:
   a) a radiation source;
   b) a detector adapted to receive radiation emitted from the radiation source to generate image data;
   c) a controller operably connected to the radiation source and the detector to control the operation of the radiation source and detector to generate the image data, the controller including a central processing unit and interconnected electronic memory unit for processing the image data from the detector;
   d) a display operably connected to the controller for presenting images formed from the image data;
   e) a user interface operably connected to the controller to enable user input to the controller; and f) an image prediction module operably connected to the controller and configured to:
      1) receive one or more prior screening images of a patient; and
      2) generate a predicted view of the patient from the one or more prior screening images for presentation on the display.

2. The radiography imaging system of claim 1, wherein the prior screening image comprises images from one or more imaging modalities.

3. The radiography imaging system of claim 1, wherein the prior screening image comprises at least one of annotations to the prior screening image and metadata of the prior screening image.

4. The radiography imaging system of claim 1, wherein the predicted view is a predicted radiography image of the patient.

5. The radiography imaging system of claim 1, wherein the predicted view is a predicted geometrical image of the patient.

6. The radiography imaging system of claim 1, wherein the prior screening image comprises at least one of a craniocaudal (CC) image of the patient, or a mediolateral oblique (MLO) image of the patient.

7. The radiography imaging system of claim 6, wherein the predicted view comprises at least one of a mediolateral (ML) view of the patient or a lateromedial (LM) view of the patient.

8. The radiography imaging system of claim 6, wherein the radiography imaging system is a mammography imaging system.

9. The radiography imaging system of claim 8, further comprising a biopsy device operably connected to the mammography imaging system to perform a diagnostic imaging procedure.

10. The radiography imaging system of claim 8, further comprising a magstand operably connected to the mammography imaging system to perform a diagnostic imaging procedure.

11. The radiography imaging system of claim 1, wherein the image prediction module is formed of an artificial intelligence.

12. A method for providing patient positioning assistance to perform a diagnostic imaging procedure on a radiography imaging system, the method comprising the steps of:
   a) providing a radiography imaging system comprising:
      i) a radiation source;
      ii) a detector;
      iii) a controller operably connected to the radiation source and the detector to control the operation of the radiation source and detector to generate the image data, the controller including a central processing unit and interconnected electronic memory unit for processing the image data from the detector;
      iv) a display operably connected to the controller for presenting images formed from the image data;
      v) a user interface operably connected to the controller to enable user input to the controller; and
      vi) an image prediction module operably connected to the controller and configured to generate a predicted view of the patient for presentation on the display from one or more prior screening images of the patient;
   b) supplying the one or more prior screening images to the image prediction module;
   c) generating the predicted view of the patient; and d) presenting the predicted view of the patient on the display.

13. The method of claim 12, wherein the step of supplying the one or more prior screening images to the image prediction module comprises supplying prior screening image from one or more imaging modalities to the image prediction module.

14. The method of claim 12, wherein the step of supplying the one or more prior screening images to the image prediction module comprises supplying at least one of a craniocaudal (CC) image of the patient, and a mediolateral oblique (MLO) image of the patient.

15. The method of claim 14, wherein the step of generating the predicted view of the patient comprises generating at least one of a mediolateral (ML) view of the patient or a lateromedial (LM) view of the patient.

16. The method of claim 15, wherein the step of generating the predicted view comprises generating a predicted radiography image of the patient.

17. The method of claim 15, wherein the step of generating the predicted view comprises generating a predicted geometrical image of the patient.

18. The method of claim 12, further comprising the steps of:
a) positioning the patient on the radiography imaging system in accordance with the prediction view; and
b) performing a diagnostic imaging procedure on the patient.

19. The method of claim 18, wherein the radiography imaging system is a mammography imaging system, and wherein the step of performing the diagnostic imaging procedure on the patient comprises at least one of:
a) performing a biopsy procedure;
b) performing a magnification imaging procedure; or
c) performing a spot compression imaging procedure.

20. The method of claim 12, wherein the step of presenting the predicted view of the patient on the display comprises presenting the one or more prior screening images on the display with the predicted view.

* * * * *